United States Patent [19]
Spiegel et al.

[11] 4,032,637
[45] June 28, 1977

[54] METHOD OF PROMOTING SLEEP

[75] Inventors: René Spiegel, Basel, Switzerland; John H. Gogerty, Randolph Township, N.J.; Dieter M. Loew, Bottmingen, Switzerland; Phillip L. Eden, Whippany, N.J.

[73] Assignees: Sandoz Ltd., Basel, Switzerland; Sandoz, Inc., E. Hanover, N.J.

[22] Filed: Oct. 31, 1974

[21] Appl. No.: 519,570

Related U.S. Application Data

[63] Continuation of Ser. No. 399,076, Sept. 20, 1973, abandoned.

[30] Foreign Application Priority Data

Sept. 26, 1972 Switzerland .................. 14031/72

[52] U.S. Cl. .............................................. 424/247
[51] Int. Cl.$^2$ ..................................... A61K 31/54
[58] Field of Search ................................... 424/247

[56] References Cited
OTHER PUBLICATIONS

Grollman, Pharmacology and Therapeutics, 6th Ed., 1965, Lea & Febiger, Phila., Pa., p. 258.
The Merck Index, 8th Ed., 1968, Merck & Co., Inc., Rahway, N.J., p. 664.

*Primary Examiner*—Jerome D. Goldberg
*Attorney, Agent, or Firm*—Gerald D. Sharkin; Robert S. Honor; Thomas O. McGovern

[57] ABSTRACT

The present invention concerns a novel therapeutic use as a sleep-promoting agent for the known pharmaceutical compound 10-[2-(1-methyl-2-piperidyl)ethyl]-2-methylsulphinylphenothiazine of the formula:

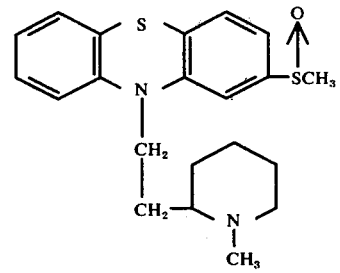

5 Claims, No Drawings

METHOD OF PROMOTING SLEEP

This is a continuation of application Ser. No. 399,076 filed Sept. 20, 1973 now abandoned.

The present invention relates to a novel therapeutic use for the known pharmaceutical compound, 10-[2-(1-methyl-2-piperidyl)ethyl]-2-methylsulphinyl-phenothiazine of formula I,

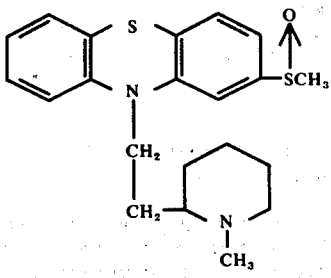

Production of the compound of formula I is disclosed, e.g. in U.S. Pat. No. 3,084,161. The compound is also known under the name Mesoridazine, and is at present indicated for use in psychiatry for the treatment of chronic schizophrenia, acute schizophrenia, alcoholism, behaviour disorders, psychically retarded patients with psychotic behaviour disorders, various psychoses, e.g. infantile and juvenile psychoses, and organic psychosyndromes with circulatory disorders.

It has now been found that the compound is useful as a sleep-promoting agent, e.g. for the treatment of severe or moderate sleep disorders, as indicated by the following tests:

In double blind clinical tests with patients between 21 and 68 years old, the compound was administered p.o. at a daily dose of 10 mg and 20 mg.

Sleep-promoting activity similar to that of known sleep-promoting agents was determined subjectively on statistical evaluation of the results of a questionnaire, concerning the time taken to fall asleep, quality of sleep, duration of sleep, frequency of waking up from sleep and condition in the morning. It was found that the sleep-promoting activity at doses of 10 mg was similar to the sleep-promoting activity at doses of 20 mg. However, incidence of hangover on the morning after, generally experienced after administration of a sleep-promoting agent, was observed only at higher doses and was in general weak and insignificant. Therefore the compound is indicated especially for use in nongeriatric patients who lead active lives and are particularly susceptible to the effects of such hangovers.

In electrophysiological tests with female patients aged between 50 and 60 years old, on p.o. administration of 10 mg of the compound daily, two sleep phases were detected:

the NREM (orthodox or slow wave) sleep, and the REM (paradoxical) sleep. The deepness of sleep increases in the NREM phase; a differentiation is made between stages 1, 2, 3 and 4.

Although the function of sleep has not been elucidated in detail, there is good evidence for the assumption that the REM sleep and the NREM sleep fulfil different functions: in stages 3 and 4 of the NREM sleep, a substantial portion of growth hormone is liberated, whereas during the course of the REM sleep phase, synthetic processes, especially in the brain, take place.

Generally on administration of known sleep-promoting agents, the REM sleep phase is proportionally reduced. When use of the sleep-promoting agent is stopped, a rebound reaction occurs which is associated with vivid dreams and nightmares.

Many sleep-promoting agents, e.g. benzodiazepines, decrease substantially stages 3 and 4 of the NREM phase after chronic intake.

However, on administration of the present compound of formula I only an insignificant distortion of the normal electrophysiological sleep pattern was determined with no or little suppression of REM and and stages 3 and 4 sleep.

The above clinical tests indicate that the present compound of formula I is well tolerated as a sleep-promoting agent by patients.

It will be appreciated that sleep-promoting activity in a phenothiazine derivative is especially interesting as such derivatives are not known to be drugs of dependence or abuse.

For the sleep-promoting use, the dosage will, of course, vary depending on the mode of administration and condition to be treated. However, in general satisfactory results are obtained when administered at a daily dosage of from about 0.05 to about 0.5 mg per kg. animal body weight, conveniently administered shortly before the normal time of sleep. For the larger mammals, the total daily dosage is in the range of from about 5 to about 25 mg, preferably from about 10 to about 20, especially from about 10 to about 15 mg, preferably administered perorally.

The compound of formula I may be administered in pharmaceutically acceptable acid addition salt form. Such acid addition salt forms exhibit the same order of activity as the free base form. Suitable acids for salt formation include hydrochloric, hydrobromic and sulphuric acids and maleic, acetic and methane sulphonic acids. The preferred pharmaceutically acceptable acid addition salt form is however the besylate salt form. Pharmaceutical compositions containing the compound of formula I in free base form or in pharmaceutically acceptable acid addition salt form, in association with a pharmaceutical carrier or diluent are known and may be prepared in conventional manner. For example, the compound may be worked up in known manner together with the usual suitable pharmaceutical adjuvants, to produce the conventional solid or liquid galenical preparations for oral, rectal or parenteral administration, e.g. tablets, capsules, dragées, drop solutions, syrups, suppositories or sterile solutions. The compound may be mixed with the adjuvants in known manner and worked up into a dose form. A preferred dose form is a solid preparation suitable for oral administration, e.g. tablets, capsules or dragées. Examples of suitable adjuvants and carrier materials for solid forms are: talc, lactose, sucrose, maize starch, polyvinyl pyrrolidone, magnesium stearate, dimethyl silicone oil, polyethylene glycol, silicic acid, stearic acid, microcrystalline cellulose and gelatine. The solid preparations may contain between 5 and 25 mg per unit dose. Suitable dose forms contain, e.g., 5, 10 or 15 mg of active compound. The pharmaceutical compositions may also contain suitable preserving, stabilizing or wetting agents, solubilizers, sweetening or colouring agents and flavourings.

The following Examples set out details of pharmaceutical compositions suitable for use in the method of the invention, it being understood that further preparations, such as those known in the literature, suitable for use in the method of the invention may be prepared by conventional techniques.

EXAMPLE 1: Tablets containing 5 mg of active compound If

| EXAMPLE 1: Tablets containing 5 mg of active compound | |
|---|---|
| Mesoridazine besylate+ | 7.05 mg |
| dimethyl silicone oil | 0.50 mg |
| polyethylene glycol | 0.50 mg |
| polyvinyl pyrrolidone | 3.00 mg |
| sucrose powder | 3.00 mg |
| talc | 3.00 mg |
| maize starch | 6.00 mg |
| lactose | 26.95 mg |
| for a tablet of | 50.00 mg |

The active compound is mixed in the usual manner with the above adjuvants and carrier materials, and the mixture is granulated and pressed into tablets in known manner.

EXAMPLE 2: Tablets containing 10 mg of active compound

| Example 2: Tablets containing 10 mg of active compound | |
|---|---|
| Mesoridazine besylate+ | 14.10 mg |
| silicic acid | 0.10 mg |
| stearic acid | 0.70 mg |
| mycrocrystalline cellulose | 5.00 mg |
| talc | 1.50 mg |
| maize starch | 2.60 mg |
| lactose | 30.50 mg |
| gelatine | 0.50 mg |
| for a tablet of | 55.00 mg |

+corresponding to 10 mg of Mesoridazine base

Admixture of the single components, granulation and tabletting may be effected in known manner.

EXAMPLE 3: Dragées containing 5 mg of active compound

Dragées may be produced in known manner from the tablets described in Example 1, using a suitable dragée coating.

EXAMPLE 4: Dragées containing 10 mg of active compound

Dragées may be produced in known manner from the tablets described in Example 2, using a suitable dragée coating.

EXAMPLE 5: Capsules containing 5 mg of active compound

| EXAMPLE 5: Capsules containing 5 mg of active compound | |
|---|---|
| Mesoridazine besylate | 7.05 mg |
| lactose pulverized | 30.00 mg |
| lactose crystalline | 116.00 mg |
| talc siliconized | 6.95 mg |
| for a capsule content of | 160.00 mg |

The components are mixed together, the mixture is sieved and filled into capsules.

EXAMPLE 6: Capsules containing 10 mg of active compound

| EXAMPLE 6: Capsules containing 10 mg of active compound | |
|---|---|
| Mesoridazine besylate | 14.10 mg |
| lactose | 302.90 mg |
| talc | 13.00 mg |
| for a capsule content of | 330.00 mg |

The components are mixed together, the mixture is sieved and filled into capsules.

EXAMPLE 7: Capsules containing 15 mg of active compound

| EXAMPLE 7: Capsules containing 15 mg of active compound | |
|---|---|
| Mesoridazine besylate | 21.15 mg |
| lactose pulverized | 75.00 mg |
| lactose crystalline | 285.00 mg |
| talc siliconized | 18.85 mg |
| for a capsule content of | 400.00 mg |

The components are mixed together, the mixture is sieved and filled into capsules.

We claim:

1. A method of promoting sleep in animals, which comprises administering to an animal suffering from insomnia a sleep promoting effective dose of 10-[2-(1-methyl-2-piperidyl)ethyl]-2-methylsulphinylphenothiazine of formula:

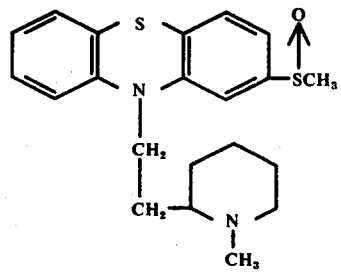

in free base form or in pharmaceutically acceptable acid addition salt form thereof.

2. A method according to claim 1, which comprises administering 10-[2-(1-methyl-2-piperidyl)-ethyl]-2-methylsulphinylphenothiazine at a daily dose of from about 0.05 to about 0.5 mg/kg animal body weight.

3. A method according to claim 2, which comprises administering 10-[2-(1-methyl-2-piperidyl)-ethyl]-2-methylsulphinylphenothiazine at a daily dose of from about 5 to about 25 mg.

4. A method of promoting sleep in mammals, which comprises administering to a mammal suffering from insomnia a daily dose of from about 10 to 20 mg. of 10-[2-(1-methyl-2-piperidyl)ethyl]-2-methylsulphinylphenothiazine of the formula:

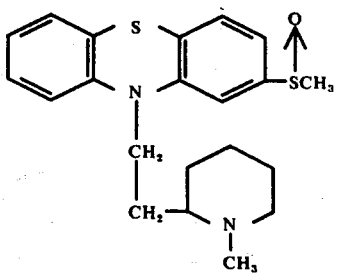

in free base form or in pharmaceutically acceptable acid addition salt form thereof.

5. A method according to claim 4, which comprises administering 10-[2-(1-methyl-2-piperidyl)-ethyl]-2-methylsulphinylphenothiazine at a daily dose of from about 10 to 15 mg.

* * * * *